United States Patent
Shih et al.

(10) Patent No.: US 6,395,928 B1
(45) Date of Patent: May 28, 2002

(54) RHODIUM-CATALYZED CARBONYLATION USING NON-ACETATE LITHIUM, SODIUM AND POTASSIUM INORGANIC SALTS AS PROMOTERS TO PRODUCE CARBOXYLIC ACIDS

(75) Inventors: Kuo-Chen Shih, Kaohsiung; Shu-Hei Wang, Hsin-Chu Hsien; Tsu-Tseng Weng; Kou-Suein Ai, both of Taipei, all of (TW)

(73) Assignee: China Petrochemical Development Corporation, Taipei (TW)

( * ) Notice: Subject to any disclaimer, the term of this patent is extended or adjusted under 35 U.S.C. 154(b) by 0 days.

(21) Appl. No.: 09/482,174

(22) Filed: Jan. 12, 2000

(30) Foreign Application Priority Data

Feb. 12, 1999 (TW) ........................ 88102251 A

(51) Int. Cl.⁷ ............................................... C07C 51/12
(52) U.S. Cl. ........................................ 562/519; 562/607
(58) Field of Search ................................. 562/519, 607

(56) References Cited

U.S. PATENT DOCUMENTS

| | | | |
|---|---|---|---|
| 3,769,329 A | 10/1973 | Paulik et al. | 260/488 K |
| 4,690,912 A | 9/1987 | Paulik et al. | 502/161 |
| 4,733,006 A | 3/1988 | Singleton et al. | 562/519 |
| 5,001,259 A | 3/1991 | Smith et al. | 562/519 |
| 5,281,751 A * | 1/1994 | Schreck | |
| 5,442,107 A | 8/1995 | Beevor et al. | 562/519 |

FOREIGN PATENT DOCUMENTS

EP        0 055 618 A1     12/1981

EP        0 153 834 A1     2/1985

OTHER PUBLICATIONS

Rhodium Complex Catalyzed Methanol Carbonylation, Hjortkjaer et al., Sep. 1975.
Applied Homogeneous Catalysis with Organometallic Compounds, vol. 1: Applications, Ch, 2.1.2, pp. 104–138, edited by Cornils et al., date unknown.

* cited by examiner

*Primary Examiner*—Gary Geist
*Assistant Examiner*—Robert W. Deemie
(74) *Attorney, Agent, or Firm*—Clifford W. Browning; Woodard, Emhardt, Naughton Moriarty & McNett

(57) ABSTRACT

The present invention relates to an improved process for producing an organic carboxylic acid having (n+1) carbon atoms by reacting an alcohol having n carbon atoms with carbon monoxide in the presence of a rhodium catalyst system. More particularly, the present invention relates to carbonylation of alcohol such as methanol catalyzed by a rhodium system to produce acetic acid. The characteristic of the present invention is the addition of a catalyst stabilizer in the reaction medium to avoid or to alleviate the precipitation of the catalyst in the liquid phase. The catalyst as used herein is a an inorganic salt of alkaline metal having the following formula (A):

$$X_nM_m \qquad\qquad (A)$$

$X = Li^+, Na^+, K^+;$
$M = CO_3^{-2}, HCO_3^-, PO_4^{-3}, HPO_4^{-2}, H_2PO_4^-, SO_4^{-2}, HSO_4^-, C_2O_4^{-2}, HC_2O_4^-, B(C_6Y_5)_4^{-1};$
$Y = H, F \text{ or } CF_3.$

12 Claims, No Drawings

RHODIUM-CATALYZED CARBONYLATION USING NON-ACETATE LITHIUM, SODIUM AND POTASSIUM INORGANIC SALTS AS PROMOTERS TO PRODUCE CARBOXYLIC ACIDS

BACKGROUND OF THE INVENTION AND PERTINENT PRIOR ART

1. Field of the Invention

The present invention relates to an improved process for producing an organic carboxylic acid having (n+1) carbon atoms by reacting an alcohol having n carbon atoms with carbon monoxide in the presence of a rhodium catalyst system. Particularly, the present invention relates to carbonylation of methanol catalyzed by a rhodium system to produce acetic acid.

2. Description of the Prior Art

It is a well known and commercialized technology for obtaining acetic acid by carbonylation of methanol with rhodium catalysts. Comparing with the early cobalt catalysts, the rhodium catalyst system has advantages of lower reaction temperature and lower carbon monoxide partial pressure as well as faster reaction rate. Typically, carbonylation of methanol with a rhodium catalyst system proceeds in a liquid phase comprising of a rhodium catalyst as dissolved therein and a promoter including methyl iodide. Related art in regard to this can be referred to the Applied Homogeneous Catalysis with Organometallic Compounds, Vol. 1, pp. 104–138 (1997).

A technology for producing acetic acid by carbonylation of methanol has been disclosed in U.S. Pat. Nos. 3,769,329 and 4,690,912 under reaction conditions as follows: reaction temperature of 180° C., pressure of monoxide between 35–70 Kg/cm², rhodium as a catalyst and methyl iodide as a promoter. It is also disclosed in these patents that the most effective solvent for producing the acetic acid is the product acetic acid per se. The main advantages of such a catalyst system are the extremely high conversion rate and selectivity (>95%). The catalyst can substantially be recycled to the reactor except some minor loss resulting from the pipe line or the pump leakage. This art can be deemed almost perfect except that for avoiding the precipitation of the rhodium catalyst and for maintaining a fairly higher reaction rate, the water content in the reaction system may have to be maintained at least 14~15 wt %. In the teachings of Hjortkjaer (Ind. Eng. Chem. Prod. Res., 1976, 15, p46), increasing the water content from 0 to 14 wt % in such a catalyst system will increase the reaction rate of methanol carbonylation correspondingly while the reaction rate is unchanged as the water content is above 14 wt %. Such a high water content will increase the expense for the separation equipment and will consume considerable energy. In recent decades, variable methods have been suggested in many patents one after another intending to enhance the solubility of the rhodium catalyst at lower water content (<14 wt %).

European Patent Publication No. 0055618 has disclosed a method for carbonylation of methanol wherein the precipitation of rhodium catalyst at lower water content is alleviated by adding organic stabilizer for the catalyst. The stabilizer as disclosed therein includes several kinds of organic compounds, alone or simultaneously, containing one or more nitrogen atoms, phosphorus atoms or carboxyl groups selected from:

(1) N,N,N$^1$,N$^1$-tetramethyl-O-phenylenediamine) and 2,3$^1$-dipyridyl;

(2) HOOC—Y$_1$—COOH and (HOOC—Y$_2$)(HOOC—Y$_3$)N—Y$_1$—N(Y$_4$—COOH)(Y$_5$—COOH),Y$_{1-5}$=(CH$_2$)m;

(3) (R$_1$)(R$_2$)P—R$_3$—P(R$_4$)(R$_5$),R$_{1-5}$=alkyl group;

U.S. Pat. No. 4,733,006 has disclosed a method of utilizing an inorganic salt additive XOAc (X=Li$^+$, Na$^+$, Ka$^+$) to alleviate the precipitation of rhodium catalyst in the reaction solution for methanol carbonylation at lower water content. However, no description regarding the influence of the inorganic salt additive to the reaction rate is mentioned through the whole patent.

It is disclosed in U.S. Pat. No. 5,001,259 that when utilizing inorganic iodide such as lithium iodide (LiI) as a stabilizer for rhodium catalyst to alleviate the precipitation of rhodium at lower water content during the carbonylation of methanol, reaction rate which is approximately comparable to the high water content (14 wt %) can be obtained. In the same patent, a kind of quaternary ammonium salt, N-methyl-picolinium iodide, is also disclosed for raising the carbonylation rate at lower water content. Unfortunately from the experiment result, it is found that the compound N-methyl-picolinium iodide forms a complex with Rh in poor solubility easily and precipitates out of the reaction solution.

The nitrogen-containing compound N-methylimidazole as disclosed in European Patent Publication No. 0153834 also forms a complex with Rh in poor solubility easily and precipitates from the reaction solution of methanol carbonylation.

In another U.S. Pat. No. 5,442,107, six kinds of heterocyclic nitrogen compounds are selected as the catalyst stabilizer for methanol carbonylation at lower water content:

(1) 2-ethyl-4-methylimidazole, (2) 4-methylpyridine, (3) 4-t-butyl-pyridine, (4) 2-hydroxylpyridine, (5) 3-hydroxylpyridine, (6) 4-hydroxylpyridine.

However, at lower water content die influence of the additive as used therein in regard to the reaction rate is not disclosed in the whole patent. It is also disclosed in the same patent the pyridine that is wholly without the substitution of alkyl group will form a complex with Rh in poor solubility easily and will precipitate from the reaction solution of methanol carbonylation at lower water content. This circumstance is similar to what happens to the organic compounds of 4-methyl-picoline and N-methylimidazole, as disclosed in the prior arts.

The prior arts as mentioned above hint several kinds of inorganic salt additives to alleviate or avoid the precipitation of rhodium catalyst when acetic acid is formed by carbonylation of methanol at lower water content. Such kind of technology therefore can save the energy consumed in the distillation process for separation the product acetic acid as well as can reduce additional processing steps such as extraction by solvents and can avoid enlarging some process equipment for the separation.

The present invention provides several kinds of inorganic salt additives different from the ones in the prior arts to lower the precipitation of rhodium catalyst when acetic acid is formed by carbonylation of methanol at lower water content. All these catalysts can be employed in either batch process or in a continuous type reactor.

The inorganic salt additive as used in the present invention is selected from the following formula (A):

$$X_nM_m \qquad (A)$$

X=Li$^+$, Na$^+$, K$^+$;

M=CO$_3^{-2}$, HCO$_3^-$, PO$_4^{-3}$, HPO$_4^{-2}$, H$_2$PO$_4^-$, SO$_4^{-2}$, HSO$_4^-$ C$_2$O$_4^{-2}$, HC$_2$O$_4^-$, B(C$_6$Y$_5$)$_4^{-1}$;

Y=H, F or CF$_3$.

Suitable amount of inorganic salt additives such as XI and XOAc (X=Li$^+$, Na$^+$, K$^+$) for use to alleviate the precipitation of the rhodium catalyst in the carbonylation of alcohol has been disclosed in prior arts. However, inorganic salt additive having formula (A) as disclosed herein has never been applied in alleviating the precipitation of the rhodium catalyst in the carbonylation of alcohol.

DETAILED DESCRIPTION AND PREFERRED EMBODIMENTS

The present invention relates to an improved process for producing an organic carboxylic acid having (n+1) carbon atoms by reacting an alcohol having n carbon atoms with carbon monoxide in the presence of a rhodium catalyst system. Particularly, the present invention relates to a process for carbonylation of methanol by the catalysis of a rhodium system to synthesize acetic acid. This process comprises directing the alcohol and/or the ester formed by said alcohol and acid along with carbon monoxide to the carbonylation reactor. Said reactor comprises the following components: (1) a rhodium catalyst, (2) the iodide derivative corresponding to the alcohol which is being reacted, (3) the ester formed by acid and alcohol, (4) the carboxylic acid, (5) at least a finite quantity of water, (6) one or more catalyst stabilizers as shown in the following formula (A):

$$X_n M_m \tag{A}$$

X=Li$^+$, Na$^+$, K$^+$;

M=CO$_3^{-2}$, HCO$_3^-$, PO$_4^{-3}$, HPO$_4^{-2}$, H$_2$PO$_4^-$, SO$_4^{-2}$, HSO$_4^-$, C$_2$O$_4^{-2}$, HC$_2$O$_4^-$, B(C$_6$Y$_5$)$_4^{-1}$;

Y=H, F or CF$_3$.

It is obvious that even in an extreme test condition with the intention of promoting rhodium precipitation, the inorganic salt additive as chosen for the present invention still will not result in a rhodium-containing complex that is partially soluble. Additional advantage of the chosen additive upon comparing with conventional preparation process is it especially effective to prevent the precipitation within the carbonylation reactor at lower water content.

In a preferred embodiment of the above described preparation process, the reacted alcohol carbonylation solution is removed from the carbonylation reactor. Carboxylic acid, rhodium catalyst and catalyst stabilizer are delivered thereafter to a location where the pressure of the carbon monoxide is lower than the carbonylation reactor, and where the separation of the carboxylic acid from other components is also exemplified. Afterwards the rhodium catalyst and the stabilizer are recycled to the carbonylation reactor. In this preferred embodiment, the characteristic of such a separation and recycle process is the coexistence of the catalyst and the stabilizer when carbon monoxide is relatively deficient.

In regard to the water content in the reactor, the present invention is even suitable for the conventional carbonylation plant for methanol, namely 14~15 wt %. However, this technology is particularly suitable for a carbonylation reactor having water content lower than the conventional method, namely 0.5–12 wt %, most preferably 1–10 wt %.

Upon concerning the alcohol having n carbon atoms, generally it can be any alcohol having 1–20 carbon atoms and having at least one hydroxyl group. More preferably, it is a mono-functional aliphatic alcohol having 1–8 carbon atoms. Most preferably, the alcohol is methanol, ethanol, or propanol, wherein methanol should be the most important material because it has been practiced for commercial use.

The whole stoichiometric equation can be represented as shown below:

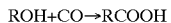

Wherein R meets the definition of the organic chain moiety as defined in the previous paragraph. The species of the carboxylic acid product can be easily deduced by alcohol that is being reacted. Taking methanol (R=CH$_3$) and ethanol (R=C$_2$H$_5$) for examples, the products are acetic acid and propionic acid, respectively.

The preparation process for the present invention can be operated in a batch process, however, it is desirably in a continuous type for most circumstances. When operated continuously, the alcohol and/or the ester formed by said alcohol and the product carboxylic acid, carbon monoxide, sufficient water to maintained at least a finite concentration of water in the carbonylation reactor, the rhodium catalyst along with iodide derivative and the catalyst stabilizer are all introduced into the carbonylation reactor. The last four components as mentioned above will not be consumed during the reaction but will be successively recycled back to the reactor from the product outlet, sometimes only minor amount may have to be replenished if in need. Corresponding to the materials successively being introduced into the carbonylation reactor, the liquid product drawn from the carbonylation reactor comprises the product acetic acid, rhodium catalyst, iodide derivatives and the catalyst stabilizer. The net effect is the carbonylation reactor reaches a stable status, and the liquid reaction medium as maintained with stable status comprises water in specified amount, stabilizer, iodide derivative, ester formed by alcohol and carboxylic acid, rhodium catalyst and carboxylic acid. In reality, the esterification between the alcohol and acid is very fast and hence only minor amount of free alcohol will be remained in the carbonylation reactor.

For the preparation process of the present invention, the amount of each component in liquid reaction medium with stable status is preferably at a range as defined below:

|  | Generally broader scope | Preferable scope |
| --- | --- | --- |
| water | 0.5–12 wt % | 1–10 wt % |
| ester formed by alcohol and acid | 0.1–10 wt % | 0.1–4 wt % |
| iodide derivative | 5–20 wt % | 10–16 wt % |
| stabilizer (moles/mole Rh) | 0.5–50 | 0.5–30 |
| rhodium catalyst (ppm) | 100–1800 | 300–1200 |

Taking carbonylation of methanol to acetic acid for example, the preferred composition of the components is water (1–10 wt %), methyl acetate (0.1–4 wt %), methyl iodide (10–16 wt %), catalyst stabilizer (0.5–30 moles/mole Rh), rhodium catalyst (300–1200 ppm) along with acetic acid.

The carbonylation reactor can be suitably maintained at a temperature of 100–200° C., and when the temperature is higher, the reaction rate is faster. The temperature is preferably at a range of 140–200° C. The pressure of carbon monoxide is maintained at 10–200 atm, more preferably at 10–100 atm.

EXAMPLE

The present invention is illustrated in the following examples which, however, are not to be construed as limiting the invention since various changes and modification within the spirit of the invention will become apparent to those skilled in the art.

The reactor as employed for the present invention comprised of a corrosion-resistant main reactor and a CO reservoir connected to the main reactor with a regulator valve between them to maintain and control the pressure in the main reactor. The Examples of the present invention were proceeded by maintaining the pressure of the reactor at 400 psi (partial pressure of CO was 173 psi). The main reactor was additionally equipped with a mechanical stirrer and an alcohol reservoir for introducing the reactants such as alcohol. Tie main reactor was heated by a heating mantle wrapping thereon, and was provided by an inlet of cooling water to control the temperature. An inlet for both the liquid reactants and the gaseous reactants was also provided for the main reactor.

During the operation of the reaction, the reactant methanol was directly added into a mixture comprising of the catalyst and the iodide promoter, where it was reacted under a constant temperature and pressure. To make quantitative comparison on the reaction rate, the rate data was expressed as a Space Time Yield (STY) as suggested by Smith B. L. et al. By which the productivity of the reaction was evaluated by calculating the quantity of acetic acid produced per unit volume per unit time. Said Space Time Yield can be obtained from the consuming rate of CO in the CO reservoir, the volume of the CO reservoir and the volume of the reaction solution. Accordingly, the changes of the CO pressure in the CO reservoir were continuously monitored during the process of the reaction for obtaining the consuming rate of CO.

Posterior to the end of the carbonylation, the temperature was lowered to room temperature and carbon monoxide was evacuated. 25 ml of reaction solution was measured and then introduced into a sealed bottle. The rhodium content in the clear solution was determined by ICP-AES.

Comparative Examples 1 and 2

For comparing with the present invention, a carbonylation experiment under lower water content wherein no additive was added was performed. The amount of each component in the reactor was 500 ppm of rhodium, 14 wt % methyl iodide and 3 wt % water. Reaction temperature was 190° C. According to the procedures as described above, the STY value as determined was about 8.1, and the rhodium as dissolved in the solution at the end of the reaction was 61% of the added amount (please see Table 1). Meanwhile, in another experiment, a known catalyst stabilizer LiI was added into the reaction mixture with reaction conditions similar to the one as described above. The molar ratio of the added LiI to the rhodium catalyst was 10, the STY value as determined after the reaction was 9.4 and the dissolved rhodium was 88% of the added amount (please see Table 1).

Examples 1–5

With reaction conditions similar to Comparative Examples 1 and 2 (the amount of each component in the reactor was 500 ppm of rhodium, 14 wt % methyl iodide, 3 wt % water with reaction temperature of 190° C.), a series of carbonylation reactions under low water content was performed, wherein the inorganic salt compounds as disclosed for the present invention, namely $Li_2C_2O_4$, $Li_2CO_3$, $Li_3PO_4$ and $NaB(C_6H_5)_4$ was added into the reaction mixture. Per the experimental procedures as described above, the STY value and the amount of rhodium as dissolved in the solution after the reaction were determined. The results in Table 1 show that the inorganic salt compounds as disclosed for the present invention had superior efficacy for alleviating the precipitation of rhodium catalyst. Meanwhile, the reaction rate in the presence of these compounds was faster than the one without adding additive and faster than the one adding the catalyst stabilizer LiI with the same mole number (please see Table 1).

TABLE 1

Examples 1–5
500 ppm of rhodium;
14 wt % methyl iodide; 3 wt % water; 190° C.

| Example | Additive | L/Rh | STY | Rh dissolved |
|---|---|---|---|---|
|  | None |  | 8.07 | 61% |
|  | LiI | 10 | 9.4 | 88% |
| 1 | $Li_2CO_3$ | 10 | 10.2 | 99% |
| 2 | $Li_2C_2O_4$ | 5 | 10.2 | 99% |
| 3 | $Li_3PO_4$ | 5 | 11.5 | 99% |
| 4 | $Li_3PO_4$ | 10 | 9.9 | 99% |
| 5 | $NaB(C_6H_5)_4$ | 10 | 10.2 | 99% |

Examples 6–10

The reaction conditions for these examples were similar to Examples 1 to 5, except the concentration of rhodium was raised to 700 ppm. The catalyst stabilizer chosen was sodium tetraphenyl borate. According to the experimental procedures as described above, the STY values of these carbonylation experiments were measured, respectively. The results shown in Table 2 indicate that the reaction rate with sodium tetraphenyl borate as additive in the presence of 6 wt % water is comparable the one that no additive is added in the presence of 14 wt % water. When it was sodium tetraphenyl borate with water content being lowered to 4%, the STY value merely lowered to 14.1; while the water content being raised to 10%, the STY value an be raised to 15.8

TABLE 2

Examples 6–10, 700 ppm of Rh, 14 wt % methyl iodide

| Example | Additive | Temperature (° C.) | Water | L/Rh | STY |
|---|---|---|---|---|---|
| 6 | sodium tetraphenyl borate | 185 | 10% | 1 | 15.8 |
| 7 | sodium tetraphenyl borate | 185 | 6% | 1 | 14.9 |
| 8 | sodium tetraphenyl borate | 185 | 4% | 1 | 14.1 |
| 9 | sodium tetraphenyl borate | 190 | 8% | 1 | 18.0 |
| 10 | None | 185 | 14% | 0 | 14.9 |

L/Rh: the molar ratio of the added additive to the rhodium catalyst

What is claimed is:

1. A process for producing organic carboxylic acid having (n+1) carbon atoms from alcohol having n carbon atoms and carbon monoxide, wherein the carbon monoxide and the alcohol are reacted in a liquid reaction medium comprising of a rhodium catalyst system, and subsequently the carboxylic acid is recovered from the resulting reaction product; during the course of carbonylation in the carbonylation reactor, the liquid reaction medium for the rhodium catalyst system comprises the following composition: (1) the rhodium catalyst, (2) the iodide derivative corresponding to the alcohol which is being reacted, (3) the ester formed by carboxylic acid and alcohol, (4) the carboxylic acid, (5) at least a finite quantity of water, (6) one or more catalyst stabilizers as shown in the following formula (A):

$$X_nM \tag{A}$$

n=1–3 or is equal to the anionic charge;
X=Li$^+$, Na$^+$ or K$^+$;
M=CO$_3^{-2}$, HCO$_3^-$, PO$_4^{-3}$, HPO$_4^{-2}$, H$_2$PO$_4^-$, SO$_4^{-2}$, HSO$_4^-$, C$_2$O$_4^{-2}$, HC$_2$O$_4^-$ or B(C$_6$Y$_5$)$_4^{-1}$;
Y=H, F or CF$_3$.

2. The process according to claim 1, wherein the specified amount of the water is maintained in 1–10 wt %.

3. The process according to claim 1, wherein the amount of rhodium is 100–1000 ppm.

4. The process according to claim 1, wherein the catalyst stabilizer is X$_2$CO$_3$, X=Li$^+$, Na$^+$ or K$^+$.

5. The process according to claim 1, wherein the catalyst stabilizer is X$_3$PO$_4$, X=Li$^+$, Na$^+$ or K$^+$.

6. The process according to claim 1, wherein the catalyst stabilizer is X$_2$C$_2$O$_4$, X=Li$^+$, Na$^+$ or K$^+$.

7. The process according to claim 1, wherein the catalyst stabilizer is XB(C$_6$H$_5$)$_4$, X=Li$^+$, Na$^+$ or K$^+$.

8. The process according to claim 1, wherein the molar ratio of the catalyst stabilizer as added to the rhodium catalyst is at least 0.5.

9. A process for producing organic carboxylic acid having (n+1) carbon atoms from alcohol having n carbon atoms and carbon monoxide, wherein the carbon monoxide and the alcohol are reacted in a liquid reaction medium comprising of a rhodium catalyst system, and subsequently the carboxylic acid is recovered from the resulting reaction product; during the course of carbonylation in the carbonylation reactor, the liquid reaction medium for the rhodium catalyst system comprises the following composition: (1) the rhodium catalyst, (2) the iodide derivative corresponding to the alcohol which is being reacted, (3) the ester formed by carboxylic acid and alcohol, (4) the carboxylic acid, (5) at least a finite quantity of water, (6) one or more catalyst stabilizers as shown in the following formula (A):

$$X_nM \tag{A}$$

n=1–3 or is equal to the anionic charge;
X=Li$^+$ or Na$^+$, K$^+$;
M=CO$_3^{-2}$, HCO$_3^-$, PO$_4^{-3}$, HPO$_4^{-2}$, H$_2$PO$_4^-$, SO$_4^{-2}$, HSO$_4^-$, C$_2$O$_4^{-2}$, HC$_2$O$_4^-$ or B(C$_6$Y$_5$)$_4^{-1}$;
Y=H, F or CF$_3$.
wherein the catalyst stabilizer is X$_2$CO$_3$, X=Li$^+$, Na$^+$ or K$^+$.

10. A process for producing organic carboxylic acid having (n+1) carbon atoms from alcohol having n carbon atoms and carbon monoxide, wherein the carbon monoxide and the alcohol are reacted in a liquid reaction medium comprising of a rhodium catalyst system, and subsequently the carboxylic acid is recovered from the resulting reaction product; during the course of carbonylation in the carbonylation reactor, the liquid reaction medium for the rhodium catalyst system comprises the following composition: (1) the rhodium catalyst, (2) the iodide derivative corresponding to the alcohol which is being reacted, (3) the ester formed by carboxylic acid and alcohol, (4) the carboxylic acid, (5) at least a finite quantity of water, (6) one or more catalyst stabilizers as shown in the following formula (A):

$$X_nM \tag{A}$$

n=1–3 or is equal to the anionic charge;
X=Li$^+$, Na$^+$ or K$^+$;
M=CO$_3^{-2}$, HCO$_3^-$, PO$_4^{-3}$, HPO$_4^{-2}$, H$_2$PO$_4^-$, SO$_4^{-2}$, HSO$_4^-$, C$_2$O$_4^{-2}$, HC$_2$O$_4^-$ or B(C$_6$Y$_5$)$_4^{-1}$;
Y=H, F or CF$_3$.
wherein the catalyst stabilizer is X$_3$PO$_4$, X=Li$^+$, Na$^+$ or K$^+$.

11. A process for producing organic carboxylic acid having (n+1) carbon atoms from alcohol having n carbon atoms and carbon monoxide, wherein the carbon monoxide and the alcohol are reacted in a liquid reaction medium comprising of a rhodium catalyst system, and subsequently the carboxylic acid is recovered from the resulting reaction product; during the course of carbonylation in the carbonylation reactor, the liquid reaction medium for the rhodium catalyst system comprises the following composition: (1) the rhodium catalyst, (2) the iodide derivative corresponding to the alcohol which is being reacted, (3) the ester formed by carboxylic acid and alcohol, (4) the carboxylic acid, (5) at least a finite quantity of water, (6) one or more catalyst stabilizers as shown in the following formula (A):

$$X_nM \tag{A}$$

n =1–3 or is equal to the anionic charge;
X=Li$^+$, Na$^+$ or K$^+$;
M=CO$_3^{-2}$, HCO$_3^-$, PO$_4^{-3}$, HPO$_4^{-2}$, H$_2$PO$_4^-$, SO$_4^{-2}$, HSO$_4^-$, C$_2$O$_4^{-2}$, HC$_2$O$_4^-$ or B(C$_6$Y$_5$)$_4^{-1}$;
Y=H,F or CF$_3$.
wherein the catalyst stabilizer is X$_2$C$_2$O$_4$, X=Li$^+$, Na$^+$or K$^+$.

12. A process for producing organic carboxylic acid having (n+1) carbon atoms from alcohol having n carbon atoms and carbon monoxide, wherein the carbon monoxide and the alcohol are reacted in a liquid reaction medium comprising of a rhodium catalyst system, and subsequently the carboxylic acid is recovered from the resulting reaction product; during the course of carbonylation in the carbonylation reactor, the liquid reaction medium for the rhodium catalyst system comprises the following composition: (1) the rhodium catalyst, (2) the iodide derivative corresponding to the alcohol which is being reacted, (3) the ester formed by carboxylic acid and alcohol, (4) the carboxylic acid, (5) at least a finite quantity of water, (6) one or more catalyst stabilizers as shown in the following formula (A):

$$X_nM \tag{A}$$

n=1–3 or is equal to the anionic charge;
X=Li$^+$, Na$^+$ or K$^+$;
M=CO$_3^{-2}$, HCO$_3^-$, PO$_4^{-3}$, HPO$_4^{-2}$, H$_2$PO$_4^-$, SO$_4^{-2}$, HSO$_4^-$, C$_2$O$_4^{-2}$, HC$_2$O$_4^-$ or B(C$_6$Y$_5$)$_4^{-1}$;
Y=H, F or CF$_3$.
wherein the catalyst stabilizer is XB(C$_6$H$_5$)$_4$, X=Li$^+$, Na$^+$ or K$^+$.

* * * * *